United States Patent
Guo et al.

(10) Patent No.: US 10,832,144 B2
(45) Date of Patent: Nov. 10, 2020

(54) EVENT SEQUENCE MANAGEMENT

(71) Applicant: International Business Machines Corporation, Armonk, NY (US)

(72) Inventors: Shi Jing Guo, Beijing (CN); Xiang Li, Beijing (CN); Hai Feng Liu, Beijing (CN); Guo Tong Xie, Beijing (CN); Shi Wan Zhao, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 806 days.

(21) Appl. No.: 15/485,950

(22) Filed: Apr. 12, 2017

(65) Prior Publication Data

US 2018/0300642 A1    Oct. 18, 2018

(51) Int. Cl.

| | |
|---|---|
| *G06Q 10/00* | (2012.01) |
| *G06Q 10/06* | (2012.01) |
| *G06F 12/08* | (2016.01) |
| *G06F 16/90* | (2019.01) |
| *G06F 17/50* | (2006.01) |
| *G06N 5/02* | (2006.01) |
| *G16H 20/10* | (2018.01) |
| *G16H 40/67* | (2018.01) |
| *G16H 50/70* | (2018.01) |
| *G16H 40/40* | (2018.01) |

(52) U.S. Cl.
CPC ............ *G06N 5/022* (2013.01); *G16H 20/10* (2018.01); *G16H 40/40* (2018.01); *G16H 40/67* (2018.01); *G16H 50/70* (2018.01)

(58) Field of Classification Search
CPC ........ G06N 5/022; G16H 40/67; G16H 50/70; G16H 20/10; G16H 40/40
USPC .................................................. 706/1–62; 1/1
See application file for complete search history.

(56) References Cited

U.S. PATENT DOCUMENTS

| | | | | |
|---|---|---|---|---|
| 9,516,377 | B1 * | 12/2016 | Chen ................ | H04N 21/2407 |
| 2002/0002564 | A1 * | 1/2002 | Munetsugu ......... | G06F 16/7834 |
| | | | | 715/204 |
| 2005/0063321 | A1 * | 3/2005 | Imai .................... | H04L 12/4641 |
| | | | | 370/256 |
| 2008/0120129 | A1 * | 5/2008 | Seubert ................ | G06Q 10/06 |
| | | | | 705/35 |
| 2014/0365529 | A1 * | 12/2014 | Aila .................... | G06F 16/9027 |
| | | | | 707/797 |

(Continued)

OTHER PUBLICATIONS

Mel, et al. "The NIST Definition of Cloud Computing". Recommendations of the National Institute of Standards and Technology, Nov. 16, 2015.

*Primary Examiner* — Brandon S Cole
(74) *Attorney, Agent, or Firm* — Joseph Petrokaitis, Esq.; McGinn IP Law Group, PLLC (57) ABSTRACT

A method, system, and computer program product for obtaining a candidate event sequence that includes at least one event for achieving a goal, obtaining a reference event sequence, the candidate event sequence comprising at least one event that is not comprised in the reference event sequence, comparing an effectiveness of the candidate event sequence on the goal and an effectiveness of the reference event sequence on the goal, and identifying the candidate event sequence as an effective sequence for achieving the goal in response to the effectiveness of the candidate event sequence being better than the effectiveness of the reference event sequence.

18 Claims, 7 Drawing Sheets

(56) References Cited

U.S. PATENT DOCUMENTS

2015/0286704 A1* 10/2015 Shyr ...................... G06F 16/35
707/737
2016/0224951 A1* 8/2016 Hoffberg .............. G06Q 20/401

* cited by examiner

EVENT SEQUENCE MANAGEMENT

BACKGROUND

The present disclosure generally relates to event sequences. Specifically, the present disclosure relates to methods and systems for event sequence management.

With the development of computer hardware and software technologies, computer aided systems now can offer management and support in every aspect of the people's life. For example, more and more industries like equipment maintenance, office automation, and patient treatment have witnessed the improvement of computer-aided software. In each area, one or more events may be executed for achieving a certain goal. For example, in the equipment maintenance, events such as base test, debug, and advanced test may be executed on the equipment for trouble shooting; in a hospital, a patient may take several treatments such as taking medicine A, B, and the like for curing a heart disease. How to measure the effectiveness of these events more accurately and effectively is now a focus of attention.

SUMMARY

In an exemplary embodiment, the present invention can provide a method for obtaining a candidate event sequence that comprises at least one event for achieving a goal, obtaining a reference event sequence, the candidate event sequence comprising at least one event that is not comprised in the reference event sequence, comparing an effectiveness of the candidate event sequence on the goal and an effectiveness of the reference event sequence on the goal, and identifying the candidate event sequence as an effective sequence for achieving the goal in response to the effectiveness of the candidate event sequence being better than the effectiveness of the reference event sequence. One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

The invention will now be described with reference to FIGS. 1-8, in which like reference numerals refer to like parts throughout. It is emphasized that, according to common practice, the various features of the drawings are not necessarily to scale. On the contrary, the dimensions of the various features can be arbitrarily expanded or reduced for clarity.

Figure 1:
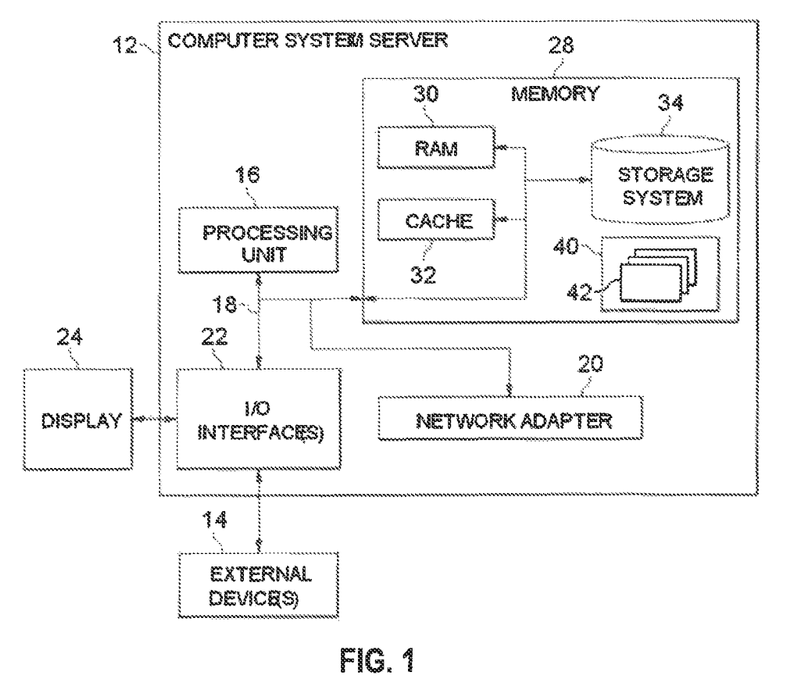
FIG. 1 depicts a cloud-computing node 10 according to an embodiment of the present invention.
Figure 3:
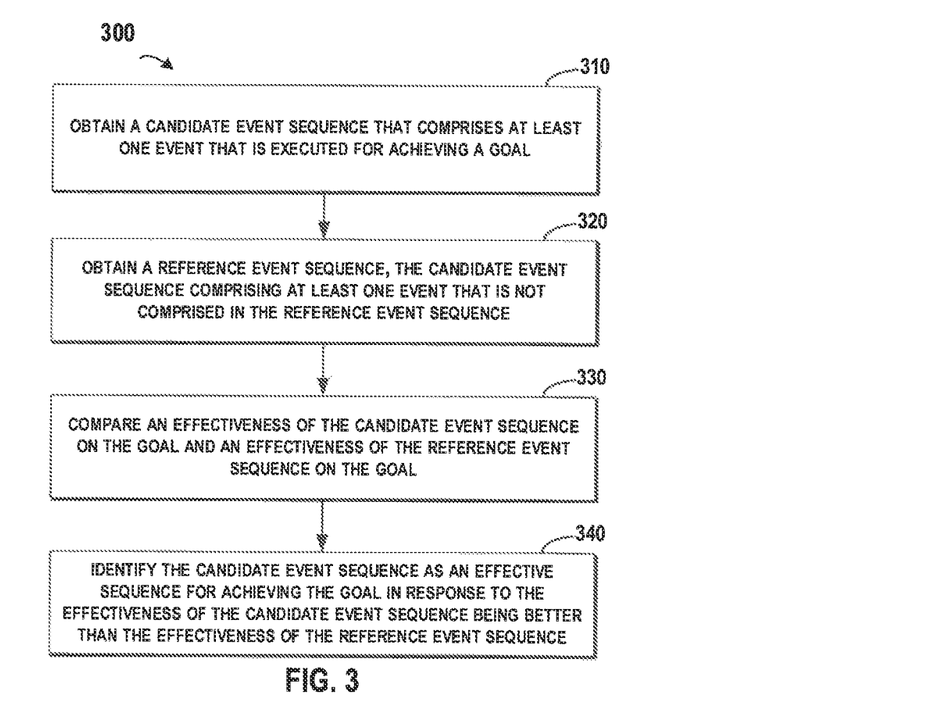
FIG. 3 schematically illustrates an example flowchart of a method for event sequent management according to one implementation of the present disclosure.

By way of introduction of the example depicted in FIG. 1, one or more computers of a computer system 12 according to an embodiment of the present invention can include a memory 28 having instructions stored in a storage system to perform the steps of FIG. 3.

Although one or more embodiments may be implemented in a cloud environment 50 (see e.g., FIG. 7), it is nonetheless understood that the present invention can be implemented outside of the cloud environment.

For the purpose of description, detailed description will be presented to various implementations of the present disclosure by means of event sequences in disease treatment throughout the context of the present disclosure. It is to be understood that although the context of the present disclosure is illustrated by taking hospital treatment as a concrete application environment, the present disclosure may further be applied to other application environments. For example, the present invention may be applied to equipment maintenance. At this point, the events may be base test, debug, and advanced test, and the goal may be remove the defects in the failed equipment.

In the event sequence, a large number of events may be executed for achieving a certain goal. Taking a hospital as an example, there may be a lot of patients with the heart disease. In order to cure these patients, doctors often follow a guideline and ask the patients to take medicines in an order such as medicines A, B, and so on. For the purpose of description, the treatment sequence such as taking medicine A, B, and so on are used as examples of the event sequences. In the present disclosure, the event A may represent that a patient takes the medicine A, the events A-B may represent that a patient takes the medicine A first and then the medicine B. In another example, the event sequence, such as the events A-B-C, may include more events. In a further example, two events may happen in parallel. The events A-(B, C) may represent that the patient takes the medicine A first, and then takes the medicines B and C at the same time. In the event sequence, the order of the events indicates a chronological order of the events.

Figure 2:
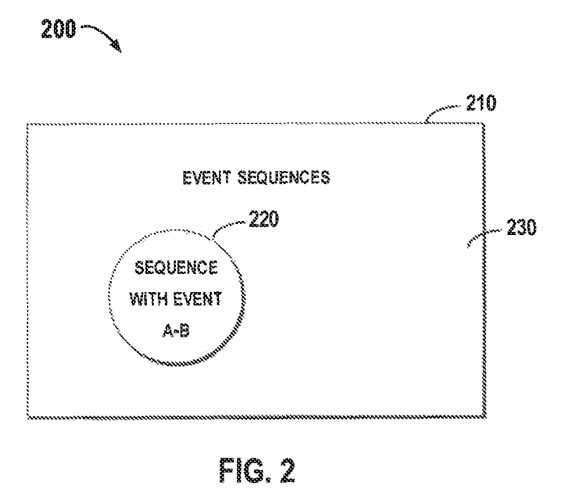
FIG. 2 schematically illustrates an example diagram for event sequence management according to one approach.

Some approaches have been proposed to perform event sequence management, and reference will be made to FIG. 2 for further information. FIG. 2 schematically illustrates an example diagram for event sequence management according to one approach. According to the approach, the patients may be divided into two groups so as to test the effectiveness of the events A-B. One group of patients (indicated by 220 in FIG. 2) may be asked to take the medicines A, and B (represented by the events A-B), and the other group of patients (indicated by 230 in FIG. 2) not taking the medicines A and B may be considered as a reference group for a comparison. Then the treatment effectiveness of two groups may be compared to see which group has a better result.

However, the approach is heavily depended on manually works and needs a lot of voluntary patients to support the comparison. When the guideline changes to a new treatment (for example, taking the medicines A-B-D), in order to test the effectiveness of the new treatment, another group of patients should take the new treatment and a new round of comparison should be performed so as to see the effect. Meanwhile, the patients in the two groups may have strong individual factors in aspects of age, gender, race, and the like. These individual factors may affect the result of the comparison. For example, different human races may have their own characteristics, so even if a treatment works effectively in Europe, there is a possibility that the treatment is ineffective in Asia. Further, various events in the event sequence do not separately exert an effect on the goal, but two or more events may jointly exert a positive or negative effect. Therefore, determining the reference group by performing a NOT operation (i.e. not taking any part of the treatment) to the group cannot accurately discover the overall effectiveness of the events.

In order to at least partially solve the above and other potential problems, a new method and system for event sequence management are proposed herein. According to implementations of the present disclosure, a method is proposed. In the method, a candidate event sequence that comprises at least one event that is executed for achieving a goal is obtained. A reference event sequence is obtained, where the candidate event sequence comprises at least one event that is not comprised in the reference event sequence. An effectiveness of the candidate event sequence on the goal is compared with an effectiveness of the reference event sequence on the goal. Then, the candidate event sequence is identified as an effective sequence for achieving the goal in response to the effectiveness of the candidate event sequence being better than the effectiveness of the reference event sequence.

With the present disclosure, the candidate event sequence may be identified as an effective one if the effectiveness of the candidate event sequence is better than that of the reference event sequence. It is to be understood that the effectiveness of both sequences may be determined from a historical data that is collected from various patients from same or different areas. Various rules may be defined to specify whether an event sequence is effective or not. According to one rule, the inpatient leaving the hospital may be considered as a positive effectiveness. Alternatively, according to another rule, the laboratory report of the patient becoming normal may be considered as a positive effectiveness. Based on the historical data of the patients, it does not need to divide the patients into groups and take different treatment for the comparison.

FIG. 3 schematically illustrates an example flowchart of a method 300 for event sequent management according to one implementation of the present disclosure. At 310, a candidate event sequence is obtained, where the candidate event sequence comprises at least one event that is executed for achieving a goal. The candidate event sequence here is the to-be-evaluated event sequence which includes a serial of events. Continuing the above example of evaluating the treatment, the candidate event sequence may include events A-B, which means that in the treatment, the patient should take the medicine A, and then take the medicine B. In another example, the candidate event sequence may only include event A, which means that the patient should take the medicine A. It is to be understood that, although the present disclosure uses taking medicine as an example of the event, the event may have other examples such as taking an operation, taking an injection, and the like.

At 320, a reference event sequence is obtained, where the candidate event sequence comprises at least one event that is not comprised in the reference event sequence. The reference event sequence may be considered as a benchmark for evaluating whether the candidate event sequence is effective or not. For the treatment, various events in an event sequence do not exert an effect on the goal separately, but two or more events may jointly exert a positive or negative effect on the goal. However, the conditional approach is based on a comparison between the group that takes the treatment and another group that does not take the treatment, thereby the joint effect of the events may be neglected.

Different from the conditional approach, the candidate event sequence of the present disclosure includes at least one event that is not comprised in the reference event sequence, instead of a comparison of the group taking the treatment and the group not taking the treatment. For example, with respect to the to-be-evaluated candidate event sequence including A-B, the reference event sequent may include the event A, the event B, or other events. With the present disclosure, a more accurate manner is proposed for determining the overall effectiveness of the events.

At 330, an effectiveness of the candidate event sequence on the goal is compared with an effectiveness of the reference event sequence on the goal. At 340, the candidate event sequence is identified as an effective sequence for achieving the goal in response to the effectiveness of the candidate event sequence on the goal being better than the effectiveness of the reference event sequence on the goal. Several aspects may be considered in comparing the effectiveness, for example, multiple samples associated with the candidate event sequence and the reference event sequence may be obtained to determine the corresponding effective.

It is to be understood that, although the candidate event sequence is obtained earlier than the time for obtaining the reference event sequence in FIG. 3, the two steps may be performed in a different order as long as the candidate event sequence comprises at least one event that is not comprised in the reference event sequence.

According to implementations of the present disclosure, in order to obtain a candidate event sequence, a hierarchical pattern may be obtained, where a node in the hierarchical pattern indicates an event sequence for achieving the goal. The candidate event sequence may be obtained by attaching a candidate event to an event sequence indicated by a leaf node in the hierarchical pattern. Details will be described with reference to FIG. 4, which schematically illustrates an example hierarchical pattern 400 for event sequent management according to one implementation of the present disclosure.

Figure 4:
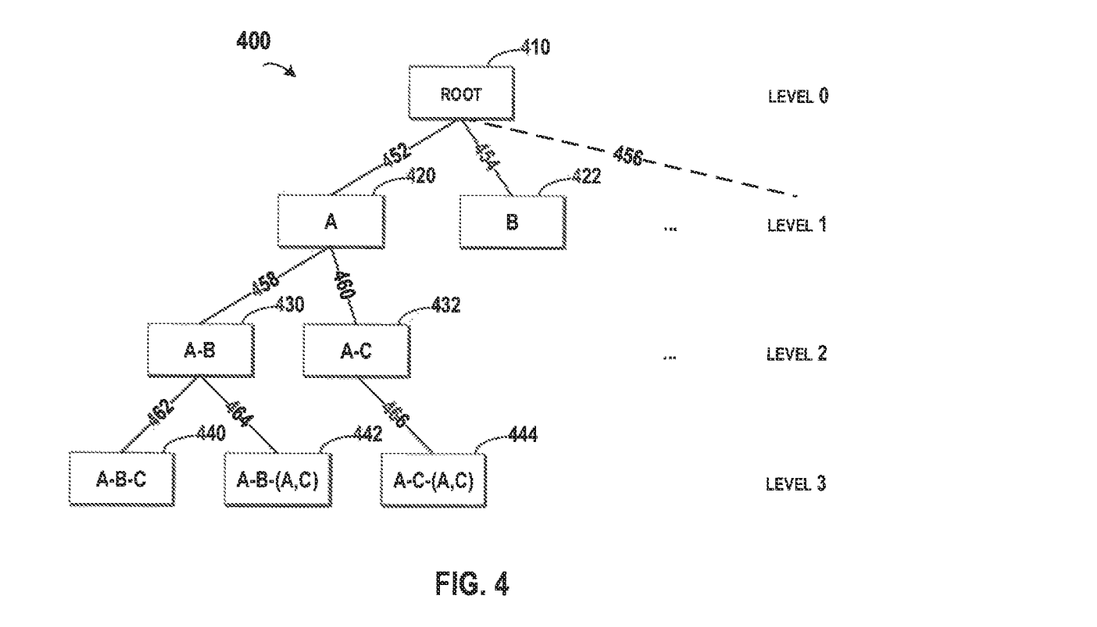
FIG. 4 schematically illustrates an example hierarchical pattern for event sequent management according to one implementation of the present disclosure.

Although the illustrated hierarchical pattern 400 includes multiple levels, initially, the hierarchical pattern 400 may be an empty tree including only one the root node. Then the hierarchical pattern may grow gradually by attaching one or more candidate events to the tree. At the beginning, the tree includes only the root node 410 at level 0, then a candidate event such as the event A indicated by the node 420 may be attached to the leaf node in the tree. At this point, the root node 410 is the leaf node and then the event A may be attached to the root node 410 at the next level (level 1). It is to be understood that the hierarchical pattern 400 is built in several rounds by attaching candidate events to the leaf nodes. In another round, another candidate node (such as the node "event B" 422) may be attached to the root node 410 at level 1.

In implementations of the present disclosure, the event sequences may be organized in the hierarchical pattern. In a next round, another node "events A-B" 430 may be attached to the node 420, where the node 430 represents an event sequence including the events A-B. As described in the preceding paragraphs, the order of A-B indicates a chronological order of the events, where the event A is executed first and the event B is executed later. After several rounds, the hierarchical pattern 400 including multiple levels (level 0 to 3) of nodes may be generated. In FIG. 4, the nodes 420 and 422 are at level 1, the nodes 430 and 432 are at level 2, and the nodes 440, 442, and 444 are at level 3. The higher the level is, the longer the length of the event sequence is. The links 452, 454, 456, 458, 460, 462, 464 and 466 indicate parent-child relationships between the two nodes connected with these links. Hereinafter, reference will be made to FIGS. 5A and 5B to describe how to determine the candidate event sequence and the reference event sequence.

Figure 5A:
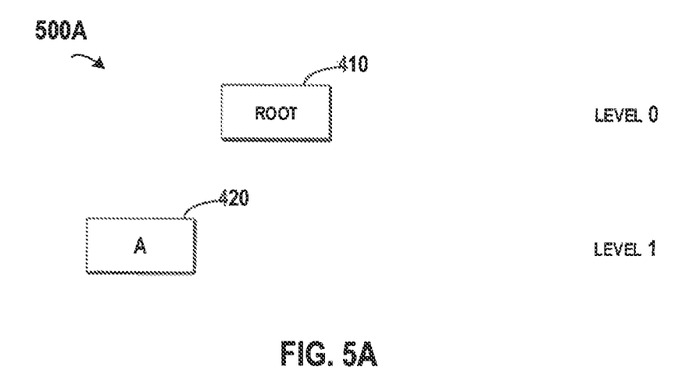
FIGS. 5A and 5B illustrate example diagrams for determining the candidate event sequence and the reference event sequence according to one implementation of the present disclosure, respectively.

In implementations of the present disclosure, the reference event sequence may be determined based on a node with a same level as the leaf node in the hierarchical pattern. FIG. 5A illustrates an example diagram for determining the candidate event sequence and the reference event sequence according to one implementation of the present disclosure, where the event A is the candidate event and the node 420 representing the candidate event may be attached to the root node 410 (the root node 410 is the leaf node currently). At this point, the event sequence includes the event A.

In implementations of the present disclosure, in order to determine the reference event sequence, any of an event sequence indicated by the leaf node or an event sequence indicated by a brother node of the leaf node may be selected as the reference event sequence. In FIG. 5A, based on the above rules, the reference event sequence may be determined based on the leaf node, i.e., the root node 410. As the root node 410 is empty at this point, the comparison may involve: a group of patients associated with the node 420 who take the medicine A, and another group of patients associated with the node 410 who do not take the medicine A.

After the comparison, if it is determined that the effectiveness of the node 420 is better than that of the node 410, then the node 420 may be attached to the node 410. At this time, the hierarchical pattern 500A will include two nodes. Based on similar processing, the hierarchical pattern 500A in FIG. 5A may gradually grow and more nodes may be added into the tree structure.

Figure 5B:
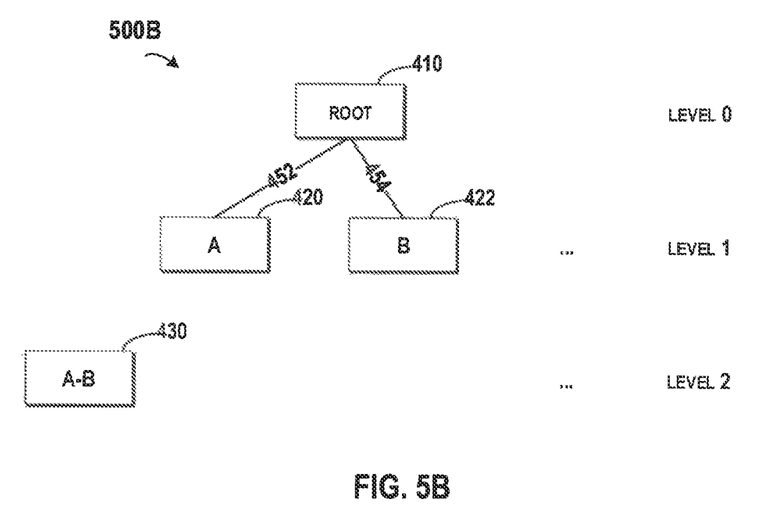

FIG. 5B illustrates another example diagrams for determining the candidate event sequence and the reference event sequence according to one implementation of the present disclosure. As illustrated in FIG. 5B, the hierarchical pattern 500B includes more nodes at various levels, where the node 420 (indicating the event A) and the node 422 (indicating the event B) are added. In FIG. 5B, the leaf nodes 420 and 422 are at the level 1. A candidate event may be added to the hierarchical pattern 410, specifically, the candidate event such as the event B may be attached to the event sequence indicated by the node 420. At this point, the event sequence indicated by the node 430 may include the events A-B.

According to the rules for determining the reference event sequence, the reference event sequence may be determined based on a node with a same level as the leaf node in the hierarchical pattern as well as a brother node of the leaf node. In FIG. 5B, the nodes 420 and 422 are the leaf node and the brother node respectively, and then the event sequence indicated by these nodes may be considered as the reference event sequence. In this example, there may be two reference event sequences: the first one includes the event A, and the second one includes the event B. In these implementations, one or more reference event sequences may be determined in the comparison, thereby the effectiveness of multiple events may be considered in determining which event sequence is effective for achieving the goal.

In implementations of the present disclosure, in order to compare an effectiveness of the candidate event sequence on the goal and a reference effectiveness of the reference event on the goal, multiple samples associated with the candidate event sequence and the reference event sequence may be utilized, such that the comparison may provide a statistical result of the effectiveness. A candidate group of candidate samples, in which the at least one event comprised in the candidate event sequence is executed, may be determined; and a reference group of reference samples, in which the at least one event comprised in the reference event sequence is executed, may be determined. Then, the effectiveness that is determined from the candidate group and the reference effectiveness that is determined from the reference group may be compared.

In implementations of the present disclosure, a plurality of patients may be used as samples associated with the candidate event sequence and the reference event sequence, and the treatment history of these patients may be traced to form the candidate and reference event sequences. Table 1 illustrates the sample data, where the column "Sample ID" indicates the ID of the patient, the column "Event" indicates the content of the event, and the column "Time" indicates the time point at which the event is executed.

TABLE 1

Sample Data

| Sample ID | Time | Event |
|---|---|---|
| k1 | 10 | A |
| k1 | 11 | B |
| k1 | 27 | C |
| k1 | 30 | C |
| k2 | 18 | B |
| k2 | 25 | C |
| k2 | 27 | D |
| ... | ... | ... |
| k10 | 10 | C |
| kn | 30 | B |

Taking the first four rows as an example, the first row indicates that the patient k1 takes the medicine A at the 10th day, the second row indicates that the patient k1 takes the medicine B at the 11th day, the third and fourth rows indicate that the patient k1 takes the medicine C at the 27th day and the 30th day respectively. In this example, the patient k1 may be considered as a sample associated with multiple event sequences including, for example, the events A, A-B, A-B-C, and so on. Similarly, the patient k2 may be a sample associated with the event sequences including the events B, B-C, B-C-D, C-D, and so on. Although Table 1 uses the day as the time unit for recording the time point of the executed event, in another example, other time units may be utilized.

The Table 1 illustrated above is just an example of the sample data, in another implementation, the sample data may include more patients associated with the multiple event sequences. For example, there may be hundreds or even more patients associated with the multiple event sequences, and the sample data of all these patients may be used for determining the effectiveness of the candidate event sequence and the reference event sequence.

Further, as the patients may have their own characteristics in aspects of age, gender, race, and the like, the effects of these aspects should be considered so as to correctly identify which event sequence is more effective based on a statistics result associated with the two sequences. As mentioned in the preceding paragraphs, the patients may have various confounding factors, and these confounding factors may affect the effectiveness. Table 2 illustrates an example confounding factors of the samples.

TABLE 2

| | Confounding Factors | | |
|---|---|---|---|
| Sample ID | Age | Gender | ... |
| k1 | 20 | Male | ... |
| k2 | 37 | Female | ... |
| ... | | | |

The confounding factors of the patients may affect the effectiveness of the treatments. For example, the medicine A might possibly be more effective to young people than the old ones. In another example, the medicine B might possibly be more effective to the male than the female. In order to reduce the effect of these confounding factors, it is desired that the samples with similar confounding factors may be selected for both the candidate event sequence and the reference event sequence.

If it is required to test the effect for curing a heart disease, and when the patients associated with the candidate event sequence are young men, then the it is desired that young men should be selected as samples for the reference event sequence, such that the side-effect caused by different confounding factors may be reduced. Otherwise, if old men are selected as samples for the reference event sequence, then bad effectiveness might possibly be caused because of poor health conditions of the old age instead of the ineffectiveness of the reference event sequence itself.

Figure 6A:
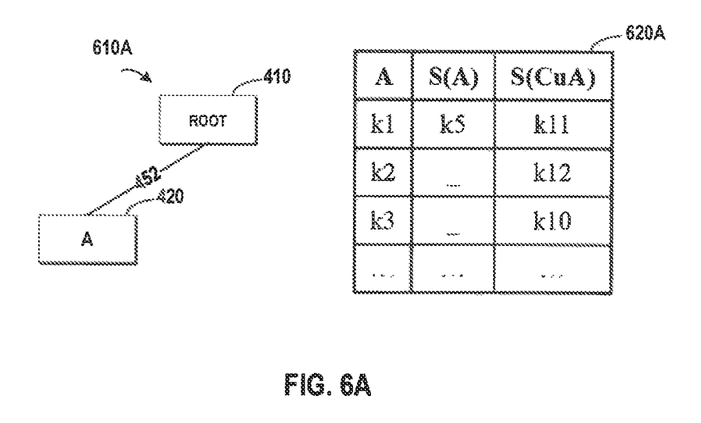
FIGS. 6A, 6B, and 6C illustrate example diagrams in various stages for obtaining the hierarchical pattern of FIG. 4 according to one implementation of the present disclosure, respectively.
Figure 6B:
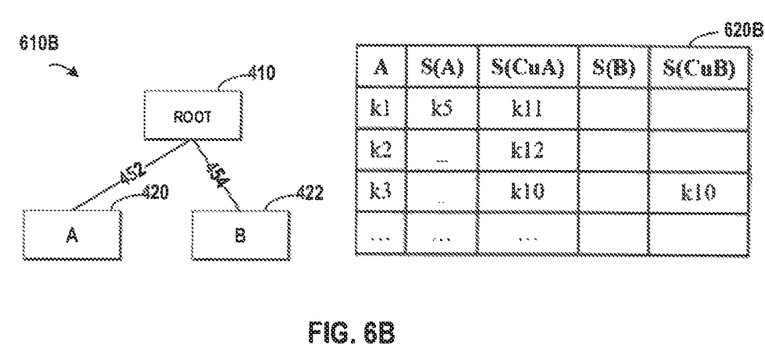
Figure 6C:
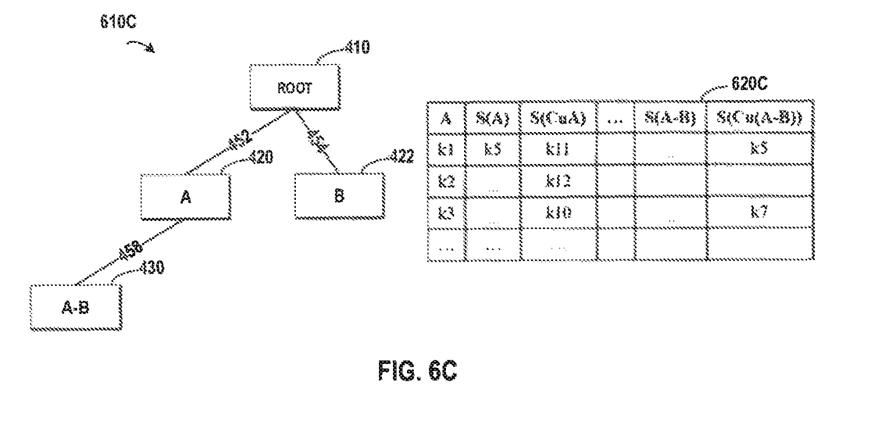

In implementations of the present disclosure, during the determining a reference group of reference samples, with respect to a sample in the group, a reference sample may be determined in the reference group based on a distance between a confounding factor of the sample and a reference confounding factor of the reference sample. In these implementations, based on the confounding factors, a similar reference sample may be determined. In other words, if age is a concerned confounding factor, based on a young patient in the candidate group associated with the candidate event sequence, another young patient may be selected as a sample for the reference group. Reference will be made to FIGS. 6A, 6B and 6C to describe how to determine the samples in the reference group.

In implementations of the present disclosure, a distance dataset may be generated for a specific sample, where the distance dataset may record a distance between the specific sample and any of at least one sample other than the specific sample. Here, the specific sample may be any one from the plurality of samples. With respect to the above example, the specific sample may be any of the patients in Table 1.

Further, the reference sample may be determined based on the distance dataset. With these implementations, the distance between the samples may be computed in advance, and then the computed distance may be directly used in determining the similar sample. The distance may be defined according to a predefined rule. For example, a Cartesian distance between the confounding factors of the two related samples may be used as the distance. Further, other types of distances may be adopted according to the requirement of the specific environment.

In one implementation, the distance dataset may be organized according to an ascending/descending order of the distances. The following Table 3 illustrates an example distance dataset, where the first column "Sample ID" indicates a sample and the second column "Ordered Samples" shows a list of samples which are ordered ascendingly according to their respective distances between their respective confounding factors and that of the sample. Taking the first row as an example, for the sample "k1," according to the distances, the samples are listed as k5, k11, k12, ..., k17 in an ascending order of the distances. In other words, k5 is the most similar sample of k1, and k11 is the second similar one.

TABLE 3

| | Distance Dataset | | | | |
|---|---|---|---|---|---|
| Sample ID | | Ordered Samples | | | |
| k1 | k5 | k11 | k12 | ... | k17 |
| k2 | k12 | k6 | k3 | ... | k11 |
| k3 | k10 | k7 | k2 | ... | k16 |
| ... | ... | ... | ... | ... | ... |
| kn | k13 | k7 | k15 | ... | k17 |

It is to be understood that the distance dataset may be generated before determining the candidate group of the candidate samples and the reference group of the reference samples. The distance dataset may be generated for all the samples; alternatively, the distance dataset may be generated for only a portion of the samples. Although Table 3 includes all the samples from k1 to kn in the first column, in another example, the distance dataset may include only some of the samples. Further, the column of "Ordered Samples" in Table 3 may include more or less sub-columns, and the content in Table 3 may be updated with the latest information of the related samples.

Based on Table 3, if k1 is in the candidate group associated with the to-be-evaluated event sequent, k5, k11, k12, ..., k17 may be tested to see which one is associated with the reference event sequence until a sample similar to k1 is found. FIGS. 6A, 6B and 6C illustrate example diagrams in various stages for obtaining the hierarchical pattern of FIG. 4 according to one implementation of the present disclosure, respectively. Referring to FIG. 6A first, the hierarchical pattern 610A illustrates an initial stage where only one node 420 is added into the hierarchical pattern 610A. At this point, the event reference includes the event A, and the samples associated with the event A may be determined according to the distance dataset of Table 3. Based on Table 1, k1 is a patient that takes the medicine A, and then k1 may be selected as a sample in the candidate group associated with the candidate event sequence.

In implementations of the present disclosure, a similarity dataset may be generated for the sample, where the similarity dataset records a candidate sample that is associated with the reference event sequence, and the candidate sample has a confounding factor similar to the sample. Further, the reference sample may be selected based on the similarity dataset.

In the similarity dataset 620A, the first column "A" represents the samples that are associated with the event A, the second column "S(A)" represents a sample "k5" who takes the medicine A. Meanwhile, "k5" is similar to the sample "k1" according to the distance dataset illustrated in Table 3. Further, the third column "S(Cu(A))" indicates a sample "k11" who does not take the medicine A. It is to be understood that "k5" is also similar to the sample "k1" according to the distance dataset illustrated in Table 3.

In implementations of the present disclosure, the similarity dataset may be updated with the event sequence and a sample that is associated with the event sequence. An example procedure is illustrated in the Table 4 for updating the similarity dataset based on a current event sequence X. In this implementation, "X" may indicate various event sequences according to various hierarchical pattern. As illustrated in Table 4, "S(X)" indicates a collection of all the samples in which the event sequence X is executed. Further, "S(Cu(X))" indicates a collection of all the samples in which the event sequence X is not executed in these samples.

TABLE 4

Example Procedure

Step 1. if the sample with the shortest distance is outside of S(X):
   record the sample in the column "S(CU(X))" in the similarity dataset, and add it to the reference group;
else:
   record the sample in the column "S(X)" in the similarity dataset;
Step 2. repeat the above "if-else" procedure until a sample outside of S(X) is found;
Step 3. record the sample in the column "S(Cu(X))" in the similarity dataset, and add it to the reference group.

Referring to the similarity dataset 620A in FIG. 6A, taking the first row "k1" as an example, "X" indicates to the event A at this point. Although "k11" is not used at the current stage, this sample may be used to determine a sample associated with an event sequence that does not include the event A. In other words, the samples in the column "S(Cu(A))" determined in this stage may be used in the future to reduce the computing workload for determining the samples for another event sequence. For the rows "k2" and "k3" in the similarity dataset 620, these situations are similar to those of the row "k1," and details will be omitted hereinafter.

As described in the preceding paragraphs, the hierarchical pattern may grow gradually, and the similarity dataset may grow together with the growth of the hierarchical pattern. FIG. 6B illustrates an example diagram another stage after the stage of FIG. 6A according to one implementation of the present disclosure. Compared with FIG. 6A, another node 422 is added to form the hierarchical pattern 610B. Referring to the similarity dataset 620B, the columns "A," "S(A)," and "S(Cu(A))" are similar to those in FIG. 6A, and the procedure for determining samples in the columns "S(B)" and "S(Cu(B))" are similar to those the columns "S(A)," and "S(Cu(A))," and the details will be omitted hereinafter.

FIG. 6C illustrates an example diagram another stage after the stage of FIG. 6B according to one implementation of the present disclosure. Based on the procedure of Table 4, another node 430 is added to form the hierarchical pattern 610C, and another two columns "S(A-B)" and S(Cu(A-B)) are attached to the end of the similarity dataset 620C. Based on similar rules, those skilled in the art may attach more columns to the similarity dataset 620C.

According to the above rules for determining the samples associated with the candidate event sequence and the reference event sequence, the effectiveness of the candidate event sequence and the effectiveness of the reference event sequence may be determined. Whether the sequence (for example, the candidate event sequence and the reference event sequence) is effective to the goal may be measured according to a predefined rule.

In one implementation, odds ratio (OR) may be determined. The odds ratio is an indicator to quantify the effectiveness of a condition on a goal. In the present disclosure, OR may be used to compare the effectiveness of the candidate event sequence and the reference event sequence. Continuing the above example, it is predefined that the inpatient leaving the hospital may be considered as a positive effectiveness. Once the samples of the candidate group associated with the candidate event sequence and the samples of the reference group associated with the reference event sequence are determined, the following number may be determined from the patient data in the hospital:

N1: the number of patients who executed the candidate event sequence and left the hospital;

N2: the number of patients who executed the candidate event sequence and did not leave the hospital;

N3: the number of patients who executed the reference event sequence and left the hospital;

N4: the number of patients who executed the reference event sequence and did not leave the hospital.

In this example, the OR may be determined based on the following equation:

$$OR = (N1*N4)/(N2*N3) \quad (1)$$

If OR>1, then it indicates that the candidate event sequence is much effective; otherwise, it indicates that the reference event sequence is much effective. It is to be understood that the above rule for determining a positive effect and the equation (1) are just examples for describing how to compare the effectiveness of the candidate event sequence and the reference event sequence. In another implementation, other rules may be utilized in the comparison. For example, in treating the patients with fever, the temperature becoming normal may be the positive effectiveness, and then the number of patients with fever and with normal temperature may be counted respectively for the candidate event sequence and the reference event sequence.

In the above implementation, although the OR may be used as an indicator for measuring the effectiveness. Because the confounding factors may affect the effectiveness of both the candidate event sequence and the reference event sequence, and sometimes the OR cannot provide an accurate measurement. In order to alleviate the effect caused by the confounding factors, an adjusted OR may be used in some implementations. In order to determine the adjusted OR, a logistic regression may be utilized and the confounding factors may be considered. The adjusted OR may reflect the effects of the confounding factors and measure the effectiveness in a more accurate manner. The present disclosure does not limit the ways for determining the adjusted OR, instead, the adjusted OR may be determined according to the algorithms that are developed previously or to be developed in the future.

In implementations of the present disclosure, the identified candidate event sequence may be attached to the leaf node in the hierarchical pattern. In these implementations, if it is determined that the effectiveness of the candidate event sequence is better than that of the reference event sequence, then the node associated with the candidate event sequence may be attached to the leaf node in the hierarchical pattern. Referring back to FIG. 5A, if the effectiveness associated with node 420 is better than that of node 410, the node 420 may be attached to the node 410, and then the hierarchical pattern 610A in FIG. 6A may be generated. Referring back to FIG. 5B, if the effectiveness associated with node 430 is better than that of node 410, the node 420 may be attached to the node 420, and then the hierarchical pattern 610C in FIG. 6C may be generated.

According to one implementation of the present disclosure, a computer-implemented method is proposed. According to the method, a candidate event sequence that comprises at least one event that is executed for achieving a goal is obtained. A reference event sequence is obtained, where the candidate event sequence comprises at least one event that is not comprised in the reference event sequence. An effectiveness of the candidate event sequence on the goal is compared with an effectiveness of the reference event sequence on the goal. Then, the candidate event sequence is identified as an effective sequence for achieving the goal in response to the effectiveness of the candidate event sequence being better than the effectiveness of the reference event sequence.

According to one implementation of the present disclosure, a computing system is proposed. The computing system comprises a computer processor coupled to a computer-readable memory unit, where the memory unit comprises instructions that when executed by the computer processor implements a method. According to the method, a candidate event sequence that comprises at least one event that is executed for achieving a goal is obtained. A reference event sequence is obtained, where the candidate event sequence comprises at least one event that is not comprised in the reference event sequence. An effectiveness of the candidate event sequence on the goal is compared with an effectiveness of the reference event sequence on the goal. Then, the candidate event sequence is identified as an effective sequence for achieving the goal in response to the effectiveness of the candidate event sequence being better than the effectiveness of the reference event sequence.

According to one implementation of the present disclosure, a computer program product is proposed. The computer program product is tangibly stored on a non-transient machine-readable medium and comprising machine-executable instructions. When the instructions are executed on an electronic device, the electronic device is caused to: obtain a candidate event sequence that comprises at least one event that is executed for achieving a goal; obtain a reference event sequence, the candidate event sequence comprising at least one event that is not comprised in the reference event sequence; compare an effectiveness of the candidate event sequence on the goal and an effectiveness of the reference event sequence on the goal; and identify the candidate event sequence as an effective sequence for achieving the goal in response to the effectiveness of the candidate event sequence being better than the effectiveness of the reference event sequence.

The present disclosure may be a system, a method, and/or a computer program product. The computer program product may include a computer readable storage medium (or media) having computer readable program instructions thereon for causing a processor to carry out aspects of the present disclosure.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring now to FIG. 1, a computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further described below, memory 28 may include a computer program product storing one or program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may be adapted for implementation in a networking environment. In some embodiments, program modules 42 are adapted to generally carry out one or more functions and/or methodologies of the present invention.

Computer system/server 12 may also communicate with one or more external devices 14 such as a keyboard, a pointing circuit, other peripherals, such as display 24, etc., and one or more components that facilitate interaction with computer system/server 12. Such communication can occur via Input/Output (I/O) interface 22, and/or any circuits (e.g., network card, modem, etc.) that enable computer system/server 12 to communicate with one or more other computing circuits. For example, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 7:
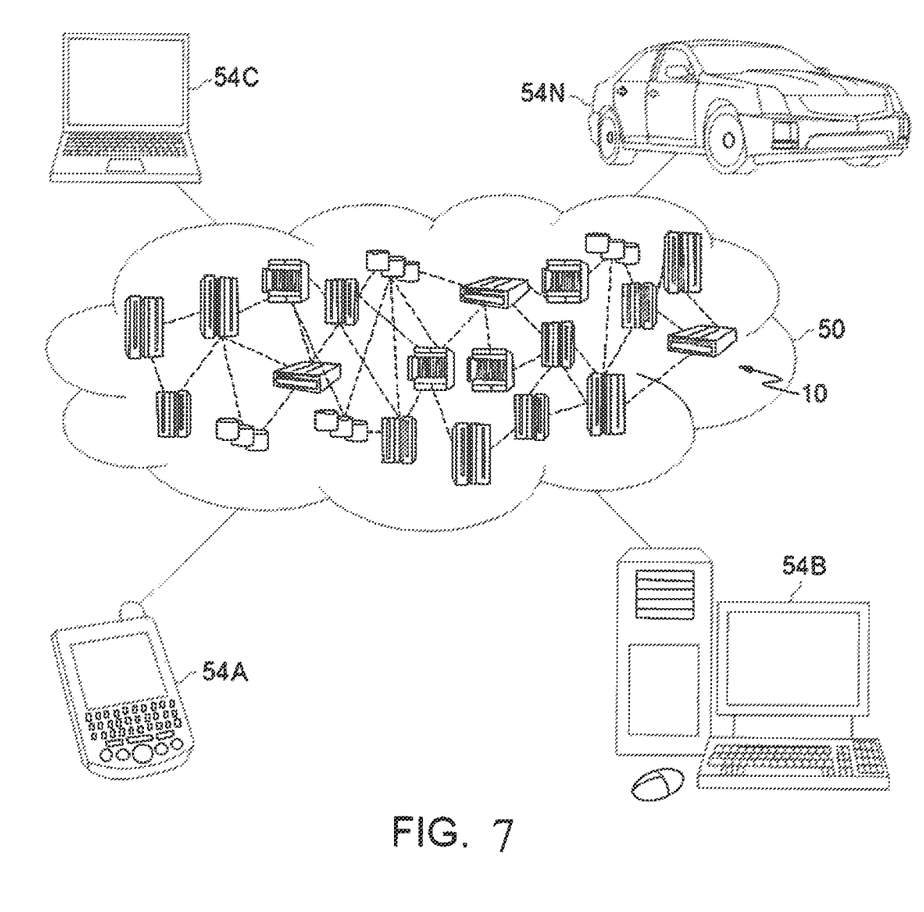
FIG. 7 depicts a cloud-computing environment 50 according to an embodiment of the present invention.

Referring now to FIG. 7, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 7 are intended to be illustrative only and that computing nodes 10 and cloud computing environment 50 can communicate with any type of computerized circuit over any type of network and/or network addressable connection (e.g., using a web browser).

Figure 8:
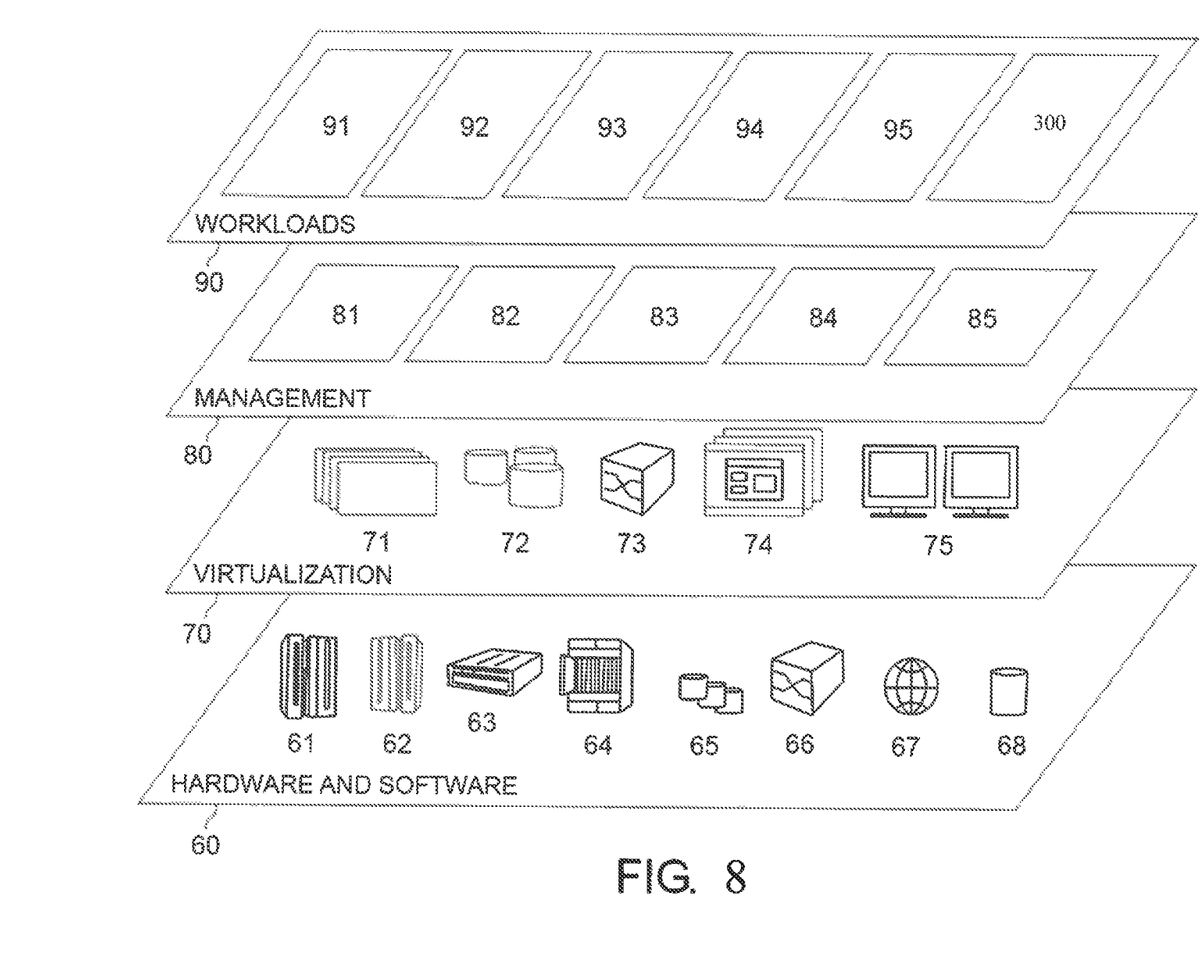
FIG. 8 depicts abstraction model layers according to an embodiment of the present invention.

Referring now to FIG. 8, an exemplary set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pro-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and method 200 in accordance with the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented method, comprising:
   obtaining a candidate event sequence that comprises at least one event for achieving a goal;
   obtaining a reference event sequence that sequentially performs a chronological order of the reference event sequence;
   comparing an effectiveness of the candidate event sequence on the goal and an effectiveness of the reference event sequence on the goal; and
   identifying the candidate event sequence as an effective sequence for achieving the goal in response to the effectiveness of the candidate event sequence being better than the effectiveness of the reference event sequence,
   wherein the candidate event sequence comprises at least one event that is not comprised in the reference event sequence, and
   wherein the comparing an effectiveness of the candidate event sequence on the goal and an effectiveness of the reference event sequence en the goal comprises:
     determining a candidate group of candidate samples on which the event comprised in the candidate event sequence is executed;
     determining a reference group of reference samples on which the event comprised in the reference event sequence is executed; and
     comparing the effectiveness that is determined from the candidate group and the reference effectiveness that is determined from the reference group.

2. The method of claim 1, wherein the obtaining a candidate event sequence comprises:
   obtaining a hierarchical pattern, a node in the hierarchical pattern indicating an event sequence for achieving the goal; and
   obtaining the candidate event sequence by attaching a candidate event to an event sequence indicated by a leaf node in the hierarchical pattern.

3. The method of claim 2, wherein the obtaining the reference event sequence comprises:
   determining the reference event sequence based on a node with a same level as the leaf node in the hierarchical pattern.

4. The method of claim 3, wherein the determining the reference event sequence comprises:
selecting, as the reference event sequence, any of an event sequence indicated by the leaf node or an event sequence indicated by a brother node of the leaf node.

5. The method according to claim 2, further comprising:
attaching the identified candidate event sequence to the leaf node in the hierarchical pattern,
wherein the candidate event sequence is obtained earlier than a time that the reference event sequence is obtained.

6. The method according to claim 1, wherein the determining a reference group of reference samples comprises:
with respect to a candidate sample in the candidate group,
determining a reference sample of the candidate sample based on a distance between a confounding factor of the candidate sample and a confounding factor of the reference sample.

7. The method according to claim 6, wherein the determining the reference sample comprises:
determining the reference sample based on a distance dataset associated with the candidate sample, wherein the distance dataset records a distance between the confounding factor of the candidate sample and the confounding factor of any of at least one sample other than the candidate sample.

8. The method according to claim 6, wherein the determining the reference sample comprises:
selecting the reference sample from a similarity dataset associated with the candidate sample, wherein the similarity dataset records samples having a confounding factor similar to that of the candidate sample.

9. The method according to claim 8, further comprising:
updating the similarity dataset based on the candidate event sequence and the sample that is associated with the candidate event sequence.

10. A computing system comprising a computer processor coupled to a computer-readable memory unit, the memory unit comprising instructions that when executed by the computer processor implements a method comprising:
obtaining a candidate event sequence that comprises at least one event for achieving a goal;
obtaining a reference event sequence that sequentially performs a chronological order of the reference event sequence;
comparing an effectiveness of the candidate event sequence on the goal and an effectiveness of the reference event sequence on the goal; and
identifying the candidate event sequence as an effective sequence for achieving the goal in response to the candidate effectiveness of the event sequence being better than the effectiveness of the reference event sequence,
wherein the candidate event sequence comprises at least one event that is not comprised in the reference event sequence, and
wherein the comparing an effectiveness of the candidate event sequence on the goal and an effectiveness of the reference event sequence on the goal comprises:
determining a candidate group of candidate samples on which the event comprised in the candidate event sequence is executed;
determining a reference group of reference samples on which the event comprised in the reference event sequence is executed; and
comparing the effectiveness that is determined from the candidate group and the reference effectiveness that is determined from the reference group.

11. The system of claim 10, wherein the obtaining a candidate event sequence comprises:
obtaining a hierarchical pattern, a node in the hierarchical pattern indicating an event sequence for achieving the goal; and
obtaining the candidate event sequence by attaching a candidate event to an event sequence indicated by a leaf node in the hierarchical pattern.

12. The system of claim 11, wherein the obtaining the reference event sequence comprises:
determining the reference event sequence based on a node with a same level as the leaf node in the hierarchical pattern.

13. The system of claim 12, wherein the determining the reference event sequence comprises:
selecting, as the reference event sequence, any of an event sequence indicated by the leaf node or an event sequence indicated by a brother node of the leaf node.

14. The system according to claim 10, wherein the determining a reference group of reference samples comprises:
with respect to a candidate sample in the candidate group,
determining a reference sample of the candidate sample based on a distance between a confounding factor of the candidate sample and a confounding factor of the reference sample.

15. The system according to claim 14, wherein the determining the reference sample comprises:
determining the reference sample based on a distance dataset associated with the candidate sample, wherein the distance dataset records a distance between the confounding factor of the candidate sample and the confounding factor of any of at least one sample other than the candidate sample.

16. The system according to claim 14, wherein the determining the reference sample comprises:
selecting the reference sample from a similarity dataset associated with the candidate sample, wherein the similarity dataset records samples having a confounding factor similar to that of the candidate sample.

17. The system according to claim 16, the method further comprising:
updating the similarity dataset based on the candidate event sequence and the sample that is associated with the candidate event sequence.

18. A computer program product being tangibly stored on a non-transient machine-readable medium and comprising machine-executable instructions, the instructions, when executed on an electronic device, causing the electronic device to:
obtain a candidate event sequence that comprises at least one event that is executed for achieving a goal;
obtain a reference event sequence that sequentially performs a chronological order of the reference event sequence;
compare an effectiveness of the candidate event sequence on the goal and an effectiveness of the reference event sequence on the goal; and
identify the candidate event sequence as an effective sequence for achieving the goal in response to the effectiveness of the candidate event sequence being better than the effectiveness of the reference event sequence, wherein the candidate event sequence comprises at least one event that is not comprised in the reference event sequence, and wherein the comparing an effectiveness of the candidate event sequence on the goal and an effectiveness of the reference event sequence on the goal comprises:
- determining a candidate group of candidate samples on which the event comprised in the candidate event sequence is executed;
- determining a reference group of reference samples on which the event comprised in the reference event sequence is executed; and
- comparing the effectiveness that is determined from the candidate group and the reference effectiveness that is determined from the reference group.

* * * * *